(12) United States Patent
Nie et al.

(10) Patent No.: US 12,318,371 B2
(45) Date of Patent: Jun. 3, 2025

(54) SUSTAINED-RELEASE MICROGEL OINTMENTS WITH HIGH DRUG LOADING AND PREPARATION METHODS AND USES THEREOF

(71) Applicant: JINAN UNIVERSITY, Guangdong (CN)

(72) Inventors: Hong Nie, Guangdong (CN); Jianhao Zhao, Guangdong (CN); Tao Zhu, Guangdong (CN); Yan Wu, Guangdong (CN); Hekun Zeng, Guangdong (CN)

(73) Assignee: JINAN UNIVERSITY, Guangdong (CN)

( * ) Notice: Subject to any disclaimer, the term of this patent is extended or adjusted under 35 U.S.C. 154(b) by 865 days.

(21) Appl. No.: 17/610,867

(22) PCT Filed: May 13, 2020

(86) PCT No.: PCT/CN2020/090012
§ 371 (c)(1),
(2) Date: Nov. 12, 2021

(87) PCT Pub. No.: WO2020/228736
PCT Pub. Date: Nov. 19, 2020

(65) Prior Publication Data
US 2022/0257573 A1    Aug. 18, 2022

(30) Foreign Application Priority Data

May 14, 2019 (CN) .......................... 201910396958.X

(51) Int. Cl.
| | | |
|---|---|---|
| *A61K 31/4375* | (2006.01) | |
| *A61K 9/06* | (2006.01) | |
| *A61K 31/352* | (2006.01) | |
| *A61K 47/36* | (2006.01) | |
| *A61K 47/38* | (2006.01) | |
| *A61P 17/04* | (2006.01) | |

(52) U.S. Cl.
CPC ............ *A61K 31/4375* (2013.01); *A61K 9/06* (2013.01); *A61K 31/352* (2013.01); *A61K 47/36* (2013.01); *A61K 47/38* (2013.01); *A61P 17/04* (2018.01)

(58) Field of Classification Search
CPC .... A61K 31/4375; A61K 9/06; A61K 31/352; A61K 47/36; A61K 47/38; A61P 17/04
See application file for complete search history.

(56) References Cited

FOREIGN PATENT DOCUMENTS

| | | | |
|---|---|---|---|
| CN | 103705535 A | * | 4/2014 |
| CN | 104906073 A | | 9/2015 |
| CN | 105412977 A | | 3/2016 |
| CN | 106990200 A | | 7/2017 |
| CN | 108371708 A | | 8/2018 |
| CN | 110974778 A | | 4/2020 |
| WO | WO-2016/162197 A1 | | 10/2016 |
| WO | WO-2019/148810 A1 | | 8/2019 |

OTHER PUBLICATIONS

Tan et al. (Biomaterials 30 (2009) 2499-2506) (Year: 2009).*

* cited by examiner

*Primary Examiner* — Daniel R Carcanague
*Assistant Examiner* — Jerica Katlynn Wilson
(74) *Attorney, Agent, or Firm* — MUNCY, GEISSLER, OLDS & LOWE, P.C.

(57) ABSTRACT

Disclosed is a sustained-release microgel ointment with high drug loading and a preparation method and use thereof. HTCC aqueous solution and HA aqueous solution are mixed uniformly to obtain the microgel aqueous solution. A drug is mixed with the microgel aqueous solution and concentrated, and a thickening agent is added and mixed evenly to obtain the sustained-release microgel ointment with high drug loading. The HA and HTCC form a microgel through electrostatic action, which is safe and convenient. The concentration step increases the concentration of the drug solution outside the microgel, which can increase the drug loading of the microgel. Drugs not loaded in the microgel inhibited the drug from being released from the microgel, prolonging the sustained release time of the microgel. The thickener transforms the drug-loaded microgel suspension into a paste, facilitating to applying the drug on the skin surface. Meanwhile, the drug added can be used at 100%, reducing the cost of microgel ointment. The ointment can be used to prepare a medicine for treating histamine-independent pruritus and analgesia.

5 Claims, 8 Drawing Sheets

CHEEK MODEL

Itching-like Scratching Behavior

Pain-like Wiping Behavior

SUSTAINED-RELEASE MICROGEL OINTMENTS WITH HIGH DRUG LOADING AND PREPARATION METHODS AND USES THEREOF

TECHNICAL FIELD

The present invention relates to the field of medicine, in particular to a sustained-release microgel ointment with high drug loading and a preparation method and use thereof.

BACKGROUND

Microgel is a micro/nano-sized hydrogel with a three-dimensional cross-linked network structure. It has the elasticity, hydrophilicity, insolubility and non-melting property of traditional hydrogels, and can also be used as a carrier for controlled release of drugs. 2-hydroxypropyltrimethyl ammonium chloride chitosan (HTCC) is a linear cationic polyelectrolyte, while hyaluronic acid (HA) is a linear anionic polyelectrolyte. Both are natural polymer materials with good biocompatibility and biodegradability and harmless to the human body, and are widely used in the field of biomedicine.

Microgels are prepared by cross-linking methods, either chemical or physical. Chemically cross-linked microgels are linked by covalent bonds, and are usually prepared by using chemical cross-linkers and initiators, the residues of which cause potential toxicity. Physically cross-linked hydrogels are often formed through physical interactions such as electrostatic interactions, hydrogen bonds, coordination bonds, hydrophobic interactions, crystallization, and others. The physical process is not involved with chemical cross-linking agents, initiators or related chemical reactions, thus is more environmentally friendly and simple.

Although microgels as drug carriers have been extensively studied, the microgels currently used for drug delivery suffer from the following shortcomings. Firstly, cross-linking agents are often added during the preparation process, presenting certain safety concerns. Secondly, in traditional methods for microgel drug loading, microgels are immersed in and then separated from the drug solution when the drug reaches a concentration balance between the inside and outside the microgel, which results in lower drug loading, leading to waste of active ingredients and increase of the preparation cost. Thirdly, the loading and release mechanisms of the drug in the microgel are mainly affected by physical diffusion driven by the difference in drug concentration inside and outside the microgel. With the low drug loading in addition to the easy diffusion of the drug due to the large concentration difference between the inside and outside of the microgel, a long-term sustained release cannot be achieved.

SUMMARY

A primary purpose of the present invention is to overcome the shortcomings and deficiencies of the prior art and provide a method for preparing a sustained-release microgel ointment with high drug loading.

A further purpose of the present invention is to provide a sustained-release microgel ointment with high drug loading obtained by the method disclosed herein.

A yet further purpose of the present invention is to provide use of the sustained-release microgel ointment with high drug loading disclosed herein.

One or more purposes of the present invention are achieved by the following technical solution.

A method for preparing a sustained-release microgel ointment with high drug loading, comprising steps of
(1) mixing a 2-hydroxypropyltrimethyl ammonium chloride chitosan (HTCC) aqueous solution with a hyaluronic acid (HA) aqueous solution homogeneously to obtain a HTCC/HA microgel aqueous solution;
(2) mixing a drug with the HTCC/HA microgel aqueous solution obtained from step (1), and concentrating the mixture; and
(3) adding a thickener and stirring well to obtain the sustained-release microgel ointment with high drug loading.

Step (1) is preferably performed by adding the HTCC aqueous solution into the HA aqueous solution under stirring.

The HTCC aqueous solution is added into the HA aqueous solution at a speed of 1 to 10 mL/h, preferably 5 to 10 mL/h.

The HTCC and the HA in step (1) have a mass ratio of 1:1 to 1:3, preferably 1:2.

Preferably, the HTCC in step (1) has a molecular weight of $2.0 \times 10^4$ to $20.0 \times 10^4$ Dalton, more preferably $10.0 \times 10^4$ Dalton.

Preferably, the HA in step (1) has a molecular weight of $5.0 \times 10^4$ to $20.0 \times 10^4$ Dalton, more preferably $10.0 \times 10^4$ Dalton.

Preferably, the HTCC aqueous solution has a concentration of 0.1 to 2.0 mg/mL, more preferably 1 mg/mL.

Preferably, the HA aqueous solution has a concentration of 0.1 to 2.0 mg/mL, more preferably 1 mg/mL.

Preferably, the mixing in step (1) is stirring.

The stirring is performed for 1 to 6 h, preferably 3 h.

The HTCC/HA microgel in step (1) has a particle size of 150 to 350 nm, and a potential of −30 to −20 mV, preferably 200 to 340 nm and −25.4 to −20.4 mV.

The drug in step (2) is preferably at least one of an alkaloid and a flavonoid, more preferably an alkaloid or a flavonoid having an effect of treating histamine-independent pruritus and analgesia.

The alkaloid is preferably at least one of oxymatrine, sophocarpine and oxysophocarpine.

The flavonoid is preferably at least one of calycosin and maackiain.

The drug is preferably a water-soluble drug.

The drug and the HTCC/HA microgel in step (2) have a mass ratio of 1:1 to 4:1, preferably 2:1.

The mixing in step (2) is preferably stirring, more preferably magnetic stirring at 200 to 400 rpm.

The stirring is performed for preferably 16 to 24 h, more preferably 20 h.

The concentrating in step (2) is preferably rotary evaporation.

The conditions of the concentrating in step (2) are 15-30 kPa under vacuum and 40-55° C., preferably 15-30 kPa under vacuum and 40-45° C., more preferably 20 kPa under vacuum and 45° C.

The mixture is preferably concentrated to 1 to 3 mg/mL, more preferably to 2 mg/mL.

The thickener in step (3) is preferably hydroxypropyl methylcellulose.

The thickener in step (3) is preferably 2% to 8% by weight based on the sustained-release microgel ointment with high drug loading, more preferably, 5 wt %.

A sustained-release microgel ointment with high drug loading, obtained by the method described herein.

A sustained-release microgel ointment comprising a drug having an effect of treating histamine-independent pruritus and analgesia, obtained by the method described herein.

The drug having an effect of treating histamine-independent pruritus and analgesia is preferably at least one of oxymatrine, sophocarpine, oxysophocarpine, calycosin and maackiain.

Use of the sustained-release microgel ointment comprising a drug having an effect of treating histamine-independent pruritus and analgesia in the preparation of a formulation for treating histamine-independent pruritus and analgesia.

The formulation for treating histamine-independent pruritus and analgesia includes, but is not limited to, external solution, lotion, liniment, ointment, paste, patch, suppository, film, capsule, emulsion, suspension, microspheres, microcapsules, nanocapsules and pills.

The invention disclosed herein has the following advantages and effects compared to the prior art.

The microgel disclosed herein is prepared by electrostatic interaction between HA and HTCC, and the high drug loading is further enhanced due to the rotary evaporation concentration and the addition of a thickener. The process does not use chemical crosslinking agents, thus is more environmentally friendly and convenient. The drug concentration of the solution outside the microgel is increased by rotary evaporation, facilitating the diffusion of the drug into the microgel, thereby the drug loading of the microgel is increased. Meanwhile, the non-loaded drug can inhibit the release of the loaded drug from the microgel, which helps prolong the sustained release.

Further, the addition of a thickener to the concentrated drug-loaded microgel suspension transforms the suspension into a paste, which facilitates smearing on the skin surface and is convenient for use. The drug added is used at 100% and the cost is thus reduced. The method can be adjusted by the amount of drug added such that most of the drugs are distributed inside the microgel, with minimum part distributed outside the microgel. The difference in the concentration of the drugs inside and outside the microgel enables the drugs in the microgel to be slowly and continuously released, reducing the side effects due to burst release. Compared with traditional ointments, the oxymatrine (see FIG. 1 for chemical structure)-loaded sustained-release microgel ointment having the effects of treating histamine-independent pruritus and analgesia disclosed herein reaches a release rate of over 90% in 48 hrs and can be fully utilized at 100%, which can reduce the times of administration while maintaining good efficacy.

The oxymatrine-loaded sustained-release microgel ointment provided by the invention has good biological safety, no skin irritation, and no damage to the human body.

DETAILED DESCRIPTION OF THE EMBODIMENTS

The embodiments of the present invention will be described in detail below in conjunction with the embodiments and the drawings, but those skilled in the art will understand that the following embodiments and examples are only used to illustrate the present invention and should not be regarded as limiting the scope of the present invention. If not otherwise specified, the normal conditions or the conditions recommended by the manufacturer shall be followed. The reagents or instruments without indication of the manufacturers are all products commercially available on the market.

Laboratory Equipment and Consumables

Pure water meter (LINIQUE-R20 type, Ruisijie Scientific Instrument Co., Ltd.), pioneer analytical balance (Ohaus Instruments (Shanghai) Co., Ltd.), vortex mixer (Vortex-Genie 2/2T type, Shanghai Lingchu Science Instrument Co., Ltd.), magnetic stirrer (type HJ-4A, Shanghai Dongxi Refrigeration Equipment Co., Ltd.), digital display intelligent temperature control magnetic stirrer (SZCL, German Bruker company), Zhongda Maidi injector (Guangzhou Zhongda Medical Equipment Co., Ltd.), laser nanoparticle size analyzer (Zetasizer-nano type, Malvern company), field emission transmission electron microscope (Tecnai G2 F20 S-TWIN 200 KV, FEI, United States), high-speed refrigerated centrifuge (USTC Innovation Co., Ltd., Zonkia Branch), ultrafiltration centrifuge tubes (15 mL, 30KD, Millipore), ultraviolet-visible spectrophotometer (UV759CRT-FS, Shanghai Youke Instrument Co., Ltd.), freeze dryer (FD-1A-50, Shanghai Bi Lang Instruments Co., Ltd.).

Experimental Drugs and Reagents

Hyaluronic acid (HA, molecular weight 5.0 to $20.0 \times 10^4$, cosmetic grade, Huaxi Freda Biomedical Co., Ltd. The HA used in the examples and comparative examples is low molecular weight sodium hyaluronate purchased from different batches), 2-hydroxypropyltrimethyl ammonium chloride chitosan (HTCC, molecular weight 2.0 to $20.0 \times 10^4$, degree of substitution 90%, Shanghai Yuanye Biological Technology Co., Ltd., the quaternary ammonium chitosan used in the examples and comparative examples are low molecular weight HTCC purchased from different batches), oxymatrine (purity 97%, Ailan (Shanghai) Chemical Technology Co., Ltd., China, CAS: 16837-52-8, Lot: CEBF150009).

Example 1

Preparation of HTCC/HA Microgel

Figure 1:
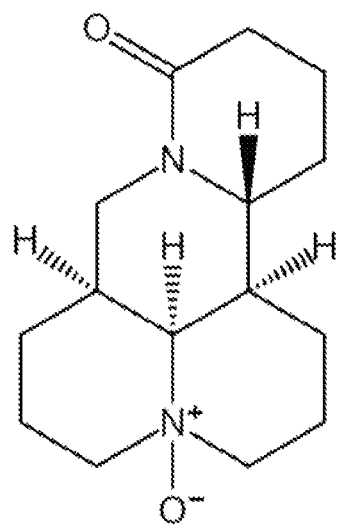
FIG. 1 shows the chemical structure of oxymatrine.
Figure 2:
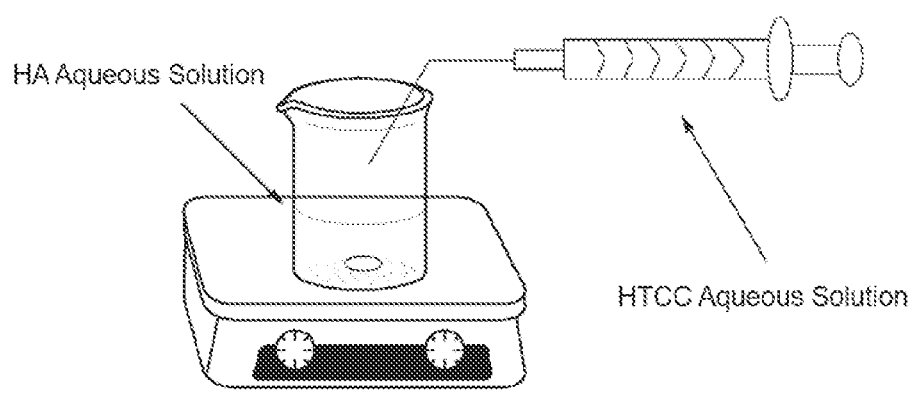
FIG. 2 is a diagram of the process for preparing the HTCC/HA microgel.
Figure 3:
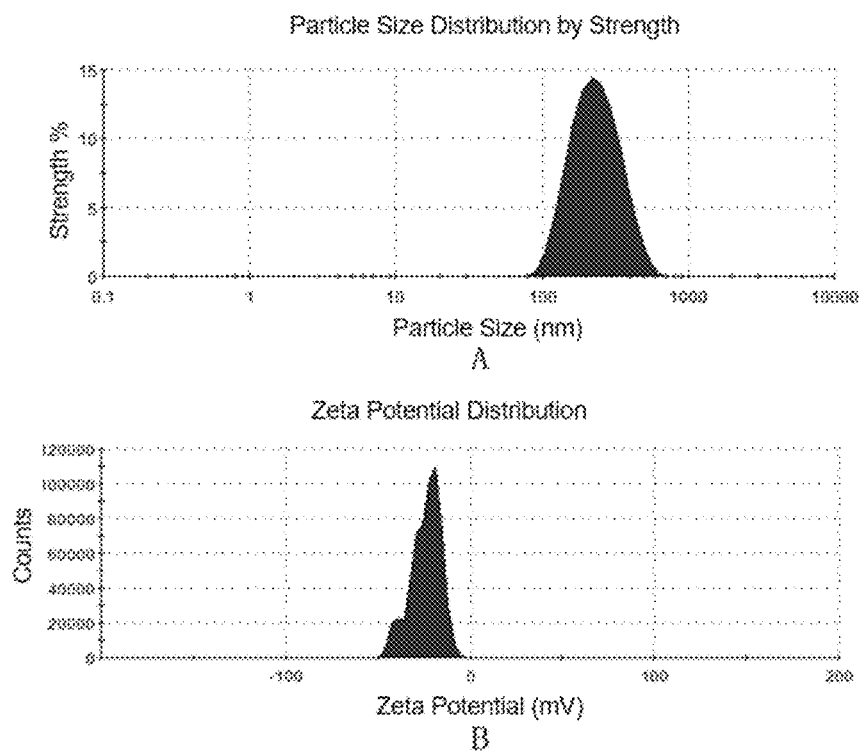
FIG. 3 is a diagram of the particle size and potential distribution of the HTCC/HA microgel. A. particle size distribution; B. potential distribution.
Figure 4:
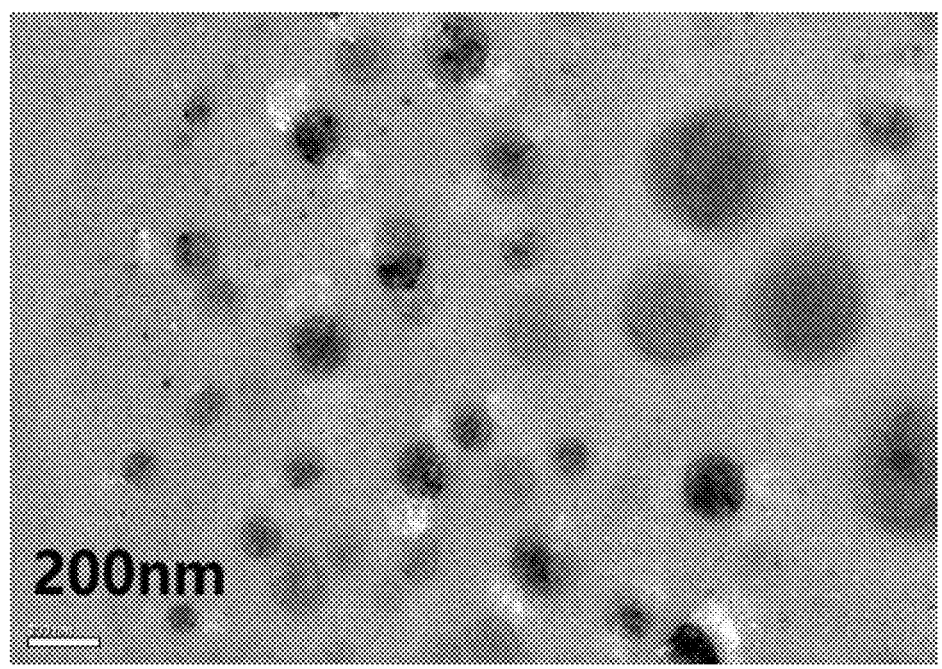
FIG. 4 is a transmission electron microscope image of the HTCC/HA microgel.

An aqueous solution of HTCC with a concentration of 1 mg/mL was prepared by dissolving the HTCC in deionized water and filtering with a filter with a pore size of 0.22 μm. The molecular weight was $10.0 \times 10^4$ as determined by gel chromatography (GPC, Waters1515, USA). An aqueous solution of HA with a concentration of 1 mg/mL was prepared by dissolving the HA in deionized water and filtering with a 0.22 μm filter. The molecular weight was $10.0 \times 10^4$ as measured by gel chromatography (GPC, Waters 1515, USA). The HTCC/HA microgel was prepared by a mass ratio of HTCC to HA at 1:2. Under magnetic stirring, 10 mL of HTCC solution was slowly injected into 20 mL of HA solution using a syringe at a rate of 5 mL/h, and stirring for 3 hours (as shown in FIG. 2) to obtain a HTCC/HA microgel aqueous solution. The particle size of the HTCC/HA microgel as measured by a Malvern laser particle sizer was 257.9±4.8 nm, and the potential was −22.3±1.9 mV (as shown in FIG. 3). The morphology of the HTCC/HA microgel was relatively uniform in size (as shown in FIG. 4), as observed under a field emission transmission electron microscope. The HTCC/HA microgel had good stability in physiological saline, and the particle size was 265.1±4.2 nm after 24h at room temperature.

Figure 5:
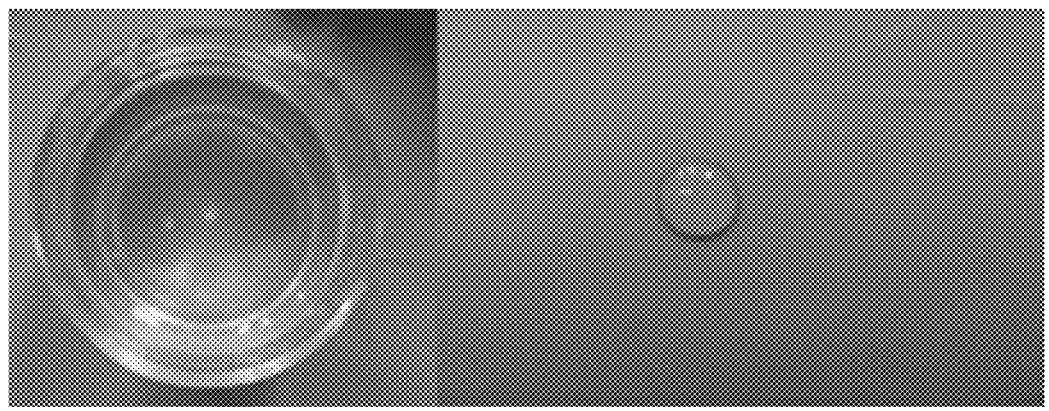
FIG. 5 shows the appearance of the HTCC/HA microgel.

Preparation of Oxymatrine-Loaded Sustained-Release Microgel Ointment 60 mg of oxymatrine (oxymatrine:microgel at 2:1) was added to the microgel aqueous solution prepared in step (1). After magnetic stirring (200-400 rpm) for 20h, the solution was concentrated to 2.0 mg/mL by a rotary evaporator at 20 kPa under vacuum and a temperature of 45° C. The supernatant drug solution was collected by centrifugation at 6000 rpm, and the distribution of the drug is 80% in the microgel and 20% in the aqueous solution as measured by an ultraviolet spectrophotometer (220 nm wavelength). The thickener hydroxypropyl methylcellulose was added according to the mass of the concentrated solution to reach a 5 wt % final concentration of the thickener. The mixture was stirred homogeneously to obtain the oxymatrine-loaded sustained-release microgel ointment (as shown in FIG. 5). The drug loading rate was 100%, of which 20% was distributed outside the microgel and 80% was distributed inside the microgel.

Figure 6:
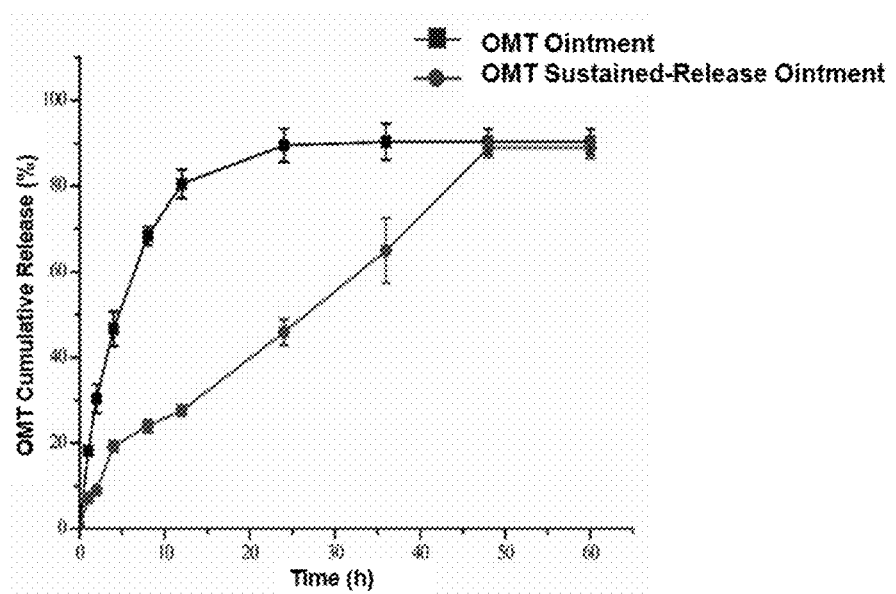
FIG. 6 shows in vitro drug release curves of the oxymatrine-loaded sustained-release microgel ointment prepared according to Example 1 and a control sample.

Drug Release Study 1.0 g of the oxymatrine-loaded sustained-release microgel ointment or control sample (prepared as same as that of oxymatrine-loaded sustained-release microgel ointment but without the microgel) was transferred to a dialysis bag (MWCO: 8000-14000), and then placed into 10 mL physiological saline solution. The dialysis was performed at 37° C., and the dialysis fluid was replaced with an equal volume of normal saline at 1h, 2h, 4h, 8h, 12h, 24 h, 36h, 48h and 60h, respectively. The absorbance of the dialysate at each time point was measured by an ultraviolet spectrophotometer at 220 nm, and the cumulative release percentage was plotted against time to obtain the in vitro release curves of the oxymatrine-loaded sustained-release microgel ointment and the control sample (FIG. 6). It can be seen from the figure that the drug release rate of the oxymatrine-loaded sustained-release microgel ointment is significantly slower than that of the control sample. The release in the control sample released 80% at 12h, while the drug release rate of the oxymatrine-loaded sustained-release microgel ointment exceeded 80% only after 48h, indicating that the microgel has a slow-release effect on drug release.

Example 2

Preparation of HTCC/HA Microgel

An aqueous solution of HTCC with a concentration of 0.1 mg/mL was prepared by dissolving the HTCC in deionized water and filtering with a filter with a pore size of 0.22 μm. The molecular weight was $20.0 \times 10^4$ as determined by gel chromatography (GPC, Waters1515, USA). An aqueous solution of HA with a concentration of 0.1 mg/mL was prepared by dissolving the HA in deionized water and filtering with a 0.22 μm filter. The molecular weight was $20.0 \times 10^4$ as measured by gel chromatography (GPC, Waters 1515, USA). The HTCC/HA microgel was prepared by a mass ratio of HTCC to HA at 1:1. Under magnetic stirring, 10 mL of HTCC solution was slowly injected into 10 mL of HA solution using a syringe at a rate of 10 mL/h, and stirring for 1 hour to obtain a HTCC/HA microgel aqueous solution. The particle size of the HTCC/HA microgel as measured by a Malvern laser particle sizer was 205.4±3.3 nm, and the potential was −23.7±1.7 mV. The morphology of the HTCC/HA microgel was of relatively uniform spherical shape, as observed under a field emission transmission electron microscope. The HTCC/HA microgel had good stability in physiological saline, and the particle size was 209.3±3.2 nm after 24h at room temperature.

Preparation of Oxymatrine-Loaded Sustained-Release Microgel Ointment 2 mg of oxymatrine-loaded (oxymatrine:microgel at 1:1) was added to the microgel aqueous solution prepared in step (1). After magnetic stirring (200-400 rpm) for 20h, the solution was concentrated to 1.0 mg/mL by a rotary evaporator at 15 kPa under vacuum and a temperature of 40° C. The supernatant drug solution was collected by centrifugation at 6000 rpm, and the distribution of the drug is 60% in the microgel and 40% in the aqueous solution as measured by an ultraviolet spectrophotometer. The thickener hydroxypropyl methylcellulose was added according to the mass of the concentrated solution to reach a final concentration of the thickener at 8 wt %. The mixture was stirred homogeneously to obtain the oxymatrine-loaded sustained-release microgel ointment. The drug loading rate was 100%, of which 40% was distributed outside the microgel and 60% was distributed inside the microgel.

Drug Release Study 1.0 g of the oxymatrine-loaded sustained-release microgel ointment or control sample (prepared as same as that of oxymatrine-loaded sustained-release microgel ointment but without the microgel) was transferred to a dialysis bag (MWCO: 8000-14000), and then placed into 10 mL physiological saline solution. The dialysis was performed at 37° C., and the dialysis fluid was replaced with an equal volume of normal saline at 1h, 2h, 4h, 8h, 12h, 24 h, 36h, 48h and 60h, respectively. The absorbance of the dialysate at each time point was measured by an ultraviolet spectrophotometer at 220 nm, and the cumulative release percentage was plotted against time to obtain the in vitro release curves of the oxymatrine-loaded sustained-release microgel ointment and the control sample. Results showed that the drug release rate of the oxymatrine-loaded sustained-release microgel ointment was significantly slower than that of the control sample. The release in the control sample released 70% at 12h, while the drug release rate of the oxymatrine-loaded sustained-release microgel ointment exceeded 70% only after 48h, indicating that the microgel has a slow-release effect on drug release.

Example 3

Preparation of HTCC/HA Microgel

An aqueous solution of HTCC with a concentration of 2.0 mg/mL was prepared by dissolving the HTCC in deionized water and filtering with a filter with a pore size of 0.22 μm. The molecular weight was $2.0 \times 10^4$ as determined by gel chromatography (GPC, Waters1515, USA). An aqueous solution of HA with a concentration of 2.0 mg/mL was prepared by dissolving the HA in deionized water and filtering with a 0.22 μm filter. The molecular weight was $5.0 \times 10^4$ as measured by gel chromatography (GPC, Waters 1515, USA). The HTCC/HA microgel was prepared by a mass ratio of HTCC to HA at 1:3. Under magnetic stirring, 10 mL of HTCC solution was slowly injected into 30 mL of HA solution using a syringe at a rate of 10 mL/h, and stirred for 6 hours to obtain a HTCC/HA microgel aqueous solution. The particle size of the HTCC/HA microgel as measured by a Malvern laser particle sizer was 325.0±13.1 nm, and the potential was −22.7±1.6 mV. The morphology of the HTCC/HA microgel was of relatively uniform spherical shape, as observed under a field emission transmission electron microscope. The HTCC/HA microgel had good stability in physiological saline, and the particle size was 335.1±4.5 nm after 24h at room temperature.

Preparation of Oxymatrine-Loaded Sustained-Release Microgel Ointment 320 mg of oxymatrine (oxymatrine:microgel at 4:1) was added to the microgel aqueous solution prepared in step (1). After magnetic stirring (200-400 rpm) for 20h, the solution was concentrated to 3.0 mg/mL by a rotary evaporator at 30 kPa under vacuum and a temperature of 45° C. The supernatant drug solution was collected by centrifugation at 6000 rpm, and the distribution of the drug was 70% in the microgel and 30% in the aqueous solution as measured by an ultraviolet spectrophotometer. The thickener hydroxypropyl methylcellulose was added according to the mass of the concentrated solution to reach a final concentration of the thickener at 2 wt %. The mixture was stirred homogeneously to obtain the oxymatrine-loaded sustained-release microgel ointment. The drug loading rate was 100%, of which 30% was distributed outside the microgel and 70% was distributed inside the microgel.

Drug Release Study 1.0 g of the oxymatrine-loaded sustained-release microgel ointment or control sample (prepared as same as that of the oxymatrine-loaded sustained-release microgel ointment but without the microgel) was transferred to a dialysis bag (MWCO: 8000-14000), and then placed into 10 mL physiological saline solution. The dialysis was performed at 37° C., and the dialysis fluid was replaced with an equal volume of normal saline at 1h, 2h, 4h, 8h, 12h, 24 h, 36h, 48h and 60h, respectively. The absorbance of the dialysate at each time point was measured by an ultraviolet spectrophotometer at 220 nm, and the cumulative release percentage was plotted against time to obtain the in vitro release curves of the oxymatrine-loaded sustained-release microgel ointment and the control sample. Results showed that the drug release rate of the oxymatrine-loaded sustained-release microgel ointment was significantly slower than that of the control sample. The release in the control sample reached 90% at 12h, while the drug release rate of the oxymatrine-loaded sustained-release microgel ointment exceeded 90% only after 48h, indicating that the microgel had a slow-release effect on drug release.

Comparative Example 1

An aqueous solution of HTCC with a concentration of 0.1 mg/mL was prepared by dissolving the HTCC in deionized water and filtering with a 0.22 μm filter. The molecular weight was $45.0 \times 10^4$ as determined by gel chromatography (GPC, Waters1515, USA). An aqueous solution of HA with a concentration of 0.1 mg/mL was prepared by dissolving the HA in deionized water and filtering with a 0.22 μm filter. The molecular weight was $60.0 \times 10^4$ as measured by gel chromatography (GPC, Waters 1515, USA). The HTCC/HA microgel was prepared by a mass ratio of HTCC to HA at 1:1. Under magnetic stirring, 10 mL of HTCC solution was slowly injected into 10 mL of HA solution using a syringe at a rate of 10 mL/h. Flocculent precipitation occurred during the preparation of the microgel, and a uniformly dispersed nano-sized microgel could not be formed.

Comparative Example 2

Preparation of HTCC/HA Microgel

An aqueous solution of HTCC with a concentration of 2.0 mg/mL was prepared by dissolving the HTCC in deionized water and filtering with a 0.22 μm filter. The molecular weight was $0.5 \times 10^4$ as determined by gel chromatography (GPC, Waters1515, USA). An aqueous solution of HA with a concentration of 2.0 mg/mL was prepared by dissolving the HA in deionized water and filtering with a 0.22 μm filter. The molecular weight was $1.0 \times 10^4$ as measured by gel chromatography (GPC, Waters 1515, USA). The HTCC/HA microgel was prepared by a mass ratio of HTCC to HA at 1:3. Under magnetic stirring, 10 mL of HTCC solution was slowly injected into 30 mL of HA solution using a syringe at a rate of 10 mL/h, stirred for 6 hours, and a HTCC/HA microgel aqueous solution was obtained. The prepared microgel had poor stability and was dissociated after being stored in physiological saline for 24 hours.

Preparation of Oxymatrine-Loaded Sustained-Release Microgel Ointment

The microgel was prepared according to the method of Example 3. However, the ointment had a poor sustained-release effect which was basically the same as the control in Examples 1-3.

Comparative Example 3

The preparation of the HTCC/HA microgel was basically the same as that of Example 1, except that when the mass ratio of HTCC and HA was at 2:1, the microgel obtained had a non-uniform particle size distribution with the particle size of 200-600 nm and a PDI greater than 0.5.

Comparative Example 4

The preparation of the HTCC/HA microgel was basically the same as that of Example 1, except that when the mass ratio of HTCC and HA was at 1:4, flocculent precipitation occurred during the preparation of the microgel.

Comparative Example 5

The preparation of the HTCC/HA microgel was basically the same as that of Example 1. The preparation of the oxymatrine-loaded sustained-release microgel ointment was basically the same as that of Example 1 except that the thickener was replaced with starch or gelatin. No obvious thickening effect was achieved for the obtained oxymatrine-loaded sustained-release ointment. The mixture after the addition of the thickener was fluidic. The sustained-release effect became poor, with the release reaching 50% in 12 hours.

Example 4

Effects of Oxymatrine-Loaded Sustained-Release Microgel Ointment on Analgesia and Treatment of Histamine-Independent Pruritus in Mice Model of Comorbid Itch and Pain Laboratory Equipment and Consumables SHIMADZU-ATY124 electronic analytical balance (Shimadzu, Japan), HDC-HS250 video camera (Panasonic, Japan), 505 vernier caliper (Mitutoyo Mfg, Japan), Blu-ray player (Panasonic, Japan), DMC-LX100 digital camera (Panasonic, Japan), 1-15K type freezing centrifuge (Sigma, Germany), ND2000C ultra-micro ultraviolet spectrophotometer (Thermo Fisher Scientific, U.S.), LightCycler480 real-time fluorescent quantitative PCR (Roche, Switzerland), Veriti® 96-Well Thermal Cycler (Applied Biosystems, USA), mouse behavioral mouse cage (Acrylic, USA), MSV269 body microscope (Leica, Germany), PCR8 strip tube (Axygen, USA, Lot: 06417002), square lens, tripod camera stand, $10 \times 10$ cm$^2$ blue PVC plastic board, $1 \times 2$ m$^2$ black light-absorbing background cloth, 1 mL disposable syringes, tweezers, ophthalmic scissors, etc.

Experimental Drugs and Reagents

Squaric acid dibutyl ester (SADBE, Tokyo Chemicals Inc, Japan, Lot: RIDHO-H, CAS: 2892-62-8); 1% sodium pentobarbital (Sigma Inc, America, Lot: 150828); compound dexamethasone acetate ointment (Huarun Sanjiu Pharmaceutical Co., Ltd., China, Lot #1804032H); sodium chloride injection (Jiangxi Kelun Pharmaceutical Co., Ltd., China, Lot: C18011407); oxymatrine (purity 97%, Ailan (Shanghai) Chemical Technology Co., Ltd., China, CAS: 16837-52-8, Lot: CEBF150009); SADBE was dissolved in acetone to prepare 1% SADBE acetone solution, and sodium pentobarbital was dissolved in physiological saline to prepare 1% sodium pentobarbital solution.

Experimental Animals and Grouping 69 male SPF C57BL/6 mice, aged 6 weeks, weighing between 20 and 25 g, purchased from Beijing Huafukang Biotechnology Co., Ltd., No. 11401300083737, license number SCXK (Beijing) 2014-0004, were raised in Experimental Animal Management Center of Jinan University, Guangdong Province, license number SYXK (Guangdong) 2017-0174, with free access to water and food. Similarly, after being adaptively fed for 1 week, the mice were randomly divided into vehicle control group (12 mice), blank ointment group (14 mice), model group (15 mice), oxymatrine-loaded sustained-release microgel ointment group (14 mice), and positive drug group (compound dexamethasone acetate ointment group, 14 mice).

Modeling and Drug Administration

Figure 7:
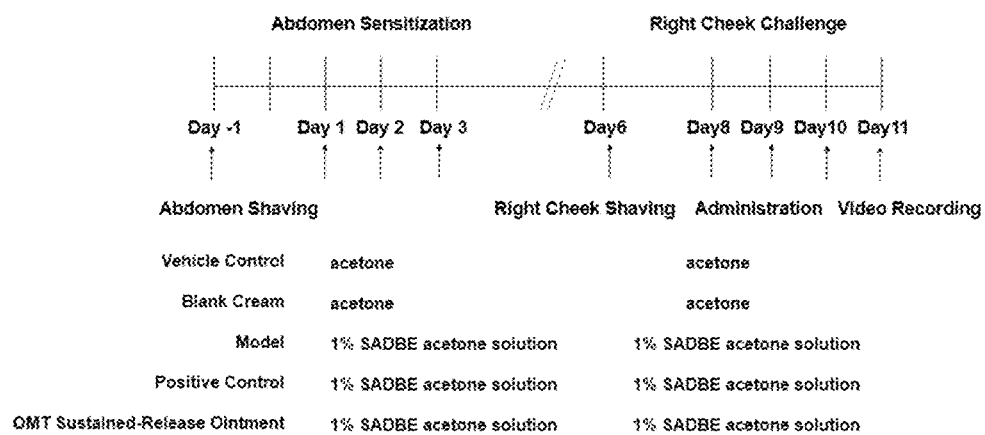
FIG. 7 is a schematic diagram of animal modeling and dosage regimen.

The mice in each group were briefly anesthetized with 1% sodium pentobarbital two days before the model was made (day −1), and then the hair on the abdomen (about $2 \times 2$ cm$^2$) of the mice was shaved with an electric knife. The mice in the vehicle control group and the blank ointment group were evenly applied with 25 μL of acetone on the shaved part of the abdomen during the sensitization period (day 1 to day 3), while the mice in the model group, the oxymatrine-loaded sustained-release microgel ointment group and the positive drug group were applied with 25 μL of 1% SADBE acetone solution on the same part. The experiment started on day −1, and the mice were placed in a special transparent acrylic cage for observing behaviors for adaptive training, once a day, two hours each time. On the 6th day of the experiment, the mice were briefly anesthetized with 1% sodium pentobarbital, and the hair on the left and right cheeks (about 1 x1 cm$^2$) of the mice was shaved off, and the thickness of the skinfold of the right cheek was measured with a vernier caliper. On days 8-9 of the experiment (challenging period), 25 μL of acetone solution was evenly applied to the shaved site on the right cheek of mice in the vehicle control group and the blank ointment group, and 254, of 1% SADBE acetone solution was applied to the same site in other groups. After 6 hours, 604, of purified water, 60 mg blank ointment, 60 mg compound dexamethasone acetate ointment (30 g: 22.5 mg), 60 mg oxymatrine-loaded sustained-release microgel ointment (prepared according to Example 2) were applied to the shaved parts of the abdomen of mice in the vehicle control group, blank ointment group, model group, positive drug group, and the oxymatrine sustained-release microgel ointment group, respectively. 30 μL of purified water, 30 mg blank ointment, 30 mg blank ointment, 30 mg compound dexamethasone acetate ointment (30 g:22.5 mg), and 30 mg oxymatrine-loaded sustained-release microgel ointment were applied on the shaved area of the right cheek in the respective group, once a day. On the 10th day of the experiment, the drugs were administered in the same manner and at the same time with days 8 and 9, once a day. The mice in each group were no longer applied acetone or 1% SADBE acetone solution on the abdomen and cheeks. On the 11th day, the mice were placed in a behavioral mouse cage to be trained for adaptability. After 30 minutes, a 1.5-hour video recording was performed for the spontaneous behaviors of mice. FIG. 7 shows the process of the behavioral experiment.

Figure 8:
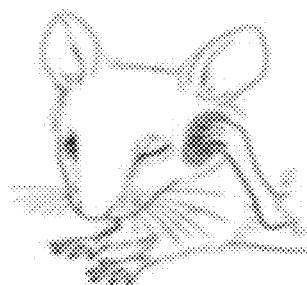
FIG. 8 shows the scratching and wiping behaviors of a mouse cheek model.
Figure 8:
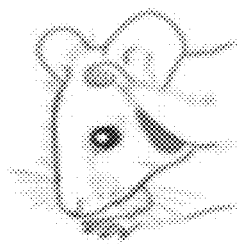

Video Recording for Behavioral Test and Behavioral Data Analysis (1) Methods for Establishment of Cheek Behavioral Model of Mouse and Video Recording The mouse cheek model has been used by more and more researchers to study the behavior of itching and pain, and the cheek model is mainly innervated by the trigeminal nerve. Statistical analysis of behaviors of itching-like scratching and pain-like wiping can be used to evaluate the effects of drugs on analgesia and the treatment of histamine-independent pruritus. Therefore, in this study, the mouse cheek model was used for pharmacodynamic evaluation of the oxymatrine-loaded sustained-release microgel ointment, as depicted in FIG. 8.

Figure 9:
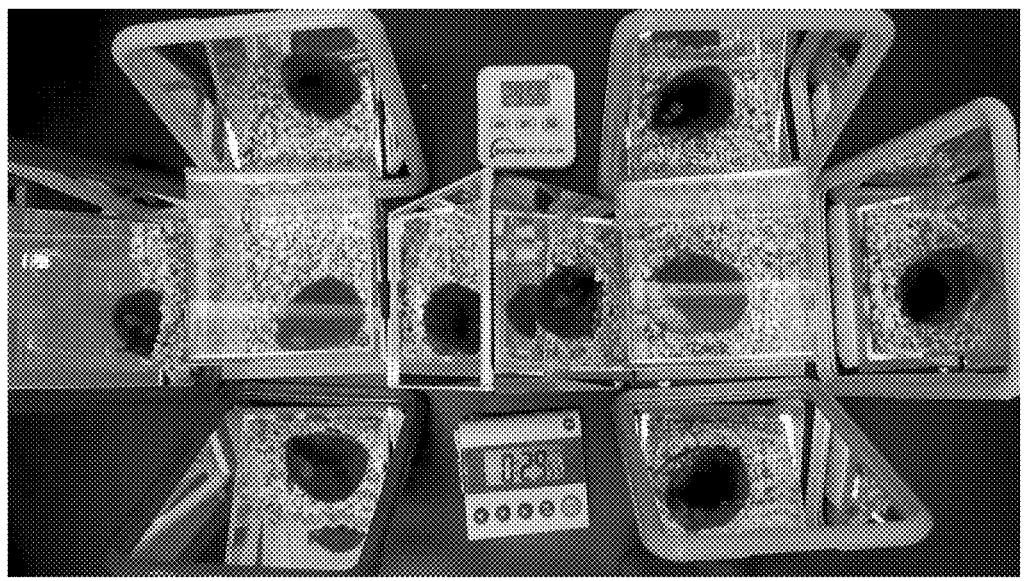
FIG. 9 shows the placement of the video equipment of the mouse cheek model.

The video recording process was described by the LaMotte research team at Yale University. Two mice were placed in their own independent and transparent acrylic adaptive cage, and a small amount of bedding was placed in each container. The size of each acrylic cage was $9 \times 9 \times 13$ $cm^3$. There were four 1 $cm^2$ circular ventilation holes on the top of the cage. There were also 5 ventilation holes of the same size at the bottom of the cage, and the bottom of each cage was affixed with a $10 \times 10$ $cm^2$ blue PVC plastic board. Finally, the two cages were placed opposite on the $1 \times 2$ $m^2$ black light-absorbing background cloth. The camera was positioned directly above the acrylic cage to ensure that the behaviors of the two mice are recorded simultaneously. Four mirrors were placed around each acrylic cage, with the angle between the mirror and the ground at about 60-75 degrees. Before recording, the positions of the mirrors were adjusted so that the spontaneous behaviors of the mice could be clearly recorded from a full range of perspectives. Two timers were placed under each camera to ensure the continuity of the recording time for subsequent statistical proofreading (FIG. 9).

Mice are very sensitive to external disturbances which can affect their behaviors. Therefore, throughout the experiment, the following measures were taken to minimize the interference of the external environment to the behavior of the mice. (1) Each mouse was individually placed in an adaptive mouse cage, and four mirrors were positioned around each mouse cage, such that no interference occurred among the mouse cages during the adaptation or the video recording phases. (2) During video recording, the ambient temperature was kept between 23-27° C., and the recording was performed between 9:00-16:00 every day. (3) A small amount of bedding which was the same as that in the feeding cage where the mice were housed was provided in the adaptive cage, such that on the one hand, the mice could better adapt to the environment of the adaptive cage, and on the other hand, it was used to absorb the urine excreted by the mice. (4) All mice were trained for adaptability for 5 days prior to formal experimentation, in order to adapt the mice to the experimental environment. (5) After the video started, the experimenters should leave the laboratory quickly to avoid disturbing the mice's behaviors. (6) The experiment was performed in a soundproof room, and pseudo-white noise was delivered from the radio to mask extraneous noises. (7) The mice were habituated to the test chamber for half an hour before video recording in the formal experimentation.

(2) Mouse Behavior Data Recording and Analysis

Itching and pain are subjective sensations. Animals cannot directly express their feelings, but they can express itching and pain through scratching and wiping. The scratching actions, especially the wiping actions, are very fast. In order to eliminate the influence of other interfering actions, the recorded video was connected to a high-resolution TV through a Blu-ray disc player for repeated slow-speed playback. Data were analyzed in a double-blind manner by researchers who did not know the grouping and the purpose of the experiment.

For the scratching behavior, it refers to the action of the mouse using the hind limbs to scratch the cheek. A bout of scratching behavior was recorded usually from the mouse raising the hind limbs to the hind limbs being put back on the ground or in the mouth. A bout of scratching behavior may include one or more repeated actions of scratching the cheek by the hind limbs, so sometimes a scratching behavior may last about 0.5-2 seconds or even longer. After the mouse scratches the cheek, there will be a small amount of debris of skin or hair residues, so mice often put their hind paws in their mouths to clean up after scratching.

For the wiping behavior, it refers to the action of the mouse using its forelimbs to wipe the cheeks. Usually, the mouse uses its unilateral forelimb to start from the back of the cheeks or the front of the ears and move rapidly toward the nose. Compared to the scratching behavior, these actions are short, gentle, and fast, and a single action lasts no more than 0.5 seconds. Mice often use the inner side of the forelimbs to wipe their cheeks. When the action occurs, the mouse's forepaws are generally held and do not touch the cheeks. The wiping behavior should be distinguished from the behavior of combing the hair. Usually, when the mouse combs the hair, both of the forelimbs wipe the cheek at the same time, or start from behind the ear, and then go through the entire cheek. Note that the behavior of alternately wiping the cheeks with the forelimbs was not recorded.

By counting the number of bouts of scratching and wiping per minute, the total number of bouts of scratching and wiping during the entire observation period was finally calculated. The mouse behavior record table is shown in Table 1 below.

TABLE 1

Date:
Mouse Number:
Starting Time:

| Period (min) | Right cheek of the mouse ||
|---|---|---|
| | Number of scratching | Number of wiping |
| 0-1 | | |
| 1-2 | | |
| 2-3 | | |
| 3-4 | | |
| 4-5 | | |
| . . . | | |
| . . . | | |
| Total | | |

Measurement of Skinfold Thickness Changes on the Challenged Part of the Right Cheek of Mice The skinfold thickness of the right cheek of the mouse, before and after the challenge, was measured using a vernier caliper by two experimenters who did not participate in the experimental design. Each mouse was measured 3 times and the mean value was calculated. The first measurement was performed after shaving on the 6th day, and the value was recorded as the skinfold thickness on the right cheek of the mouse before the challenge. The second measurement was performed after the video recording was finished on the 11th day, and the value was recorded as the skinfold thickness on the right cheek of the mouse after challenge and administration. By subtracting the value of the second measurement from the value of the first measurement, the change of the skinfold thickness at the challenged part of the right cheek of the mouse can be obtained.

Measurement of Mouse Spleen and Thymus Index

The mice were sacrificed by cervical dislocation. The spleen and thymus of the mice were completely removed, and weighted with an analytical electronic balance. The weights of the spleen (mg) and the thymus (mg) per 10 g of body weight of the mouse were used as the spleen index and thymus index, respectively.

HE Staining and Toluidine Blue Staining of the Challenged Skin on the Right Cheek of the Mouse Mice were sacrificed by cervical dislocation, the challenged area on the right cheek of the mice was cleaned. Then a small opening was cut in the lower part of the challenged skin on the right cheek of the mouse along the horizontal direction, and the skin was separated with a 10 cm sharp curved surgical scissor. The skin was peeled off with a tweezer, and cut off with an ophthalmological scissor (about 1 $cm^2$ in area). The skin was washed in normal saline, absorbed with filter paper, fixed in 4% paraformaldehyde solution, and embedded in conventional paraffin wax. A series of 5 μm thick slices were cut in the middle of the skin along the horizontal direction for Hematoxylin Eosin (HE) and toluidine blue (TB) staining, in order to observe the skin structure.

Statistics Analysis

All data were presented as mean±S.E.M. Data were analyzed via one-way ANOVA with Dunnett t3 test (in the case of uneven variance) using the SPSS18.0 software. $P<0.05$ was considered statistically significant.

Results

Figure 10:
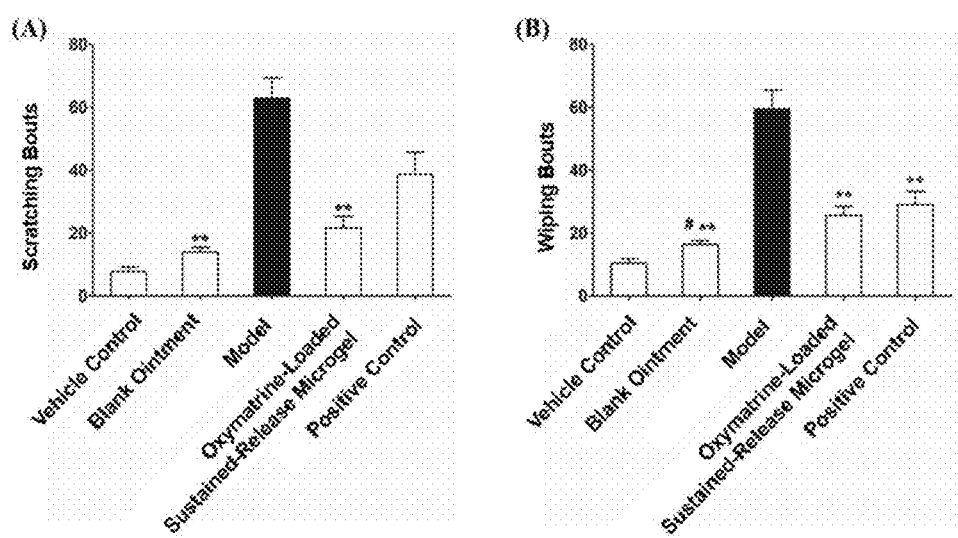
FIG. 10 is a graph showing the effect of the oxymatrine-loaded sustained-release microgel ointment on scratching and wiping behaviors of mice model of comorbid itch and pain.

FIG. 10 shows the total number of bouts of scratching and wiping behaviors directed to the right cheek within 90 minutes in the oxymatrine-loaded sustained-release microgel ointment experiment. Compared with the vehicle control group, the scratching behavior of mice in the blank ointment group was not significantly different, while the wiping behavior was significantly increased ($p<0.05$). Compared with the model group, the bouts of scratching in the blank ointment group and the oxymatrine-loaded sustained-release microgel ointment group were significantly reduced ($p<0.01$), and the bouts of scratching in the positive drug group had a tendency to decrease. The wiping behaviors of mice in the blank ointment group, the oxymatrine-loaded sustained-release microgel ointment group and the positive drug group were significantly reduced ($p<0.01$).

Figure 11:
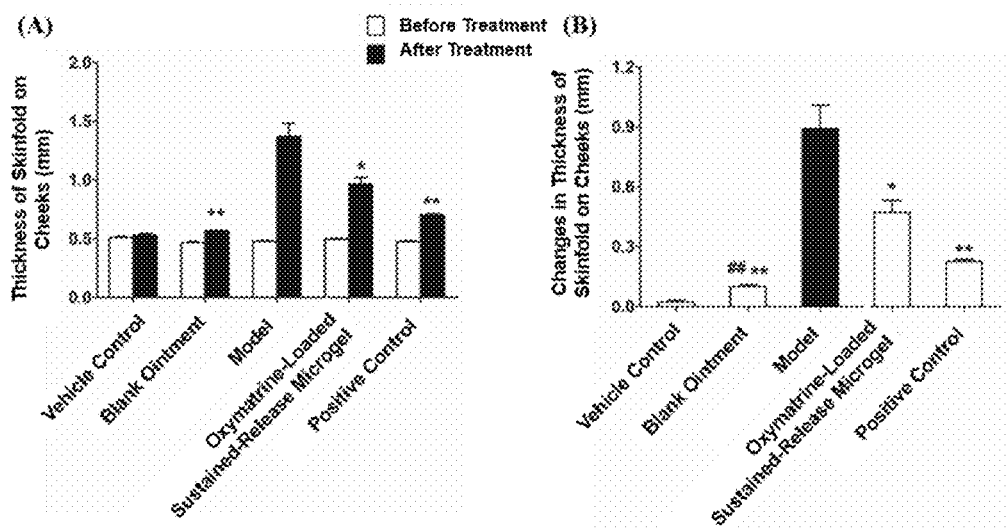
FIG. 11 is a graph showing the effect of the oxymatrine-loaded sustained-release microgel ointment on the skinfold thickness of the right cheek in mice model of comorbid itch and pain. Inset A is a histogram that shows the skinfold thickness of the right cheek before and after administration. Inset B is a histogram that shows the changes in the skinfold thickness of the cheeks of each group of mice.

FIG. 11 shows the changes in skinfold thickness at the right cheek of mice in the experiment of oxymatrine-loaded sustained-release microgel ointment. Compared with the vehicle control group, the difference in cheek skin thickness of mice in the blank ointment group increased significantly ($p<0.05$). Compared with the model group, the difference in skin thickness of the right cheek of the mice in the blank ointment group, the oxymatrine-loaded sustained-release microgel ointment group and positive drug group showed a very significant decrease ($p<0.01$).

Figure 12:
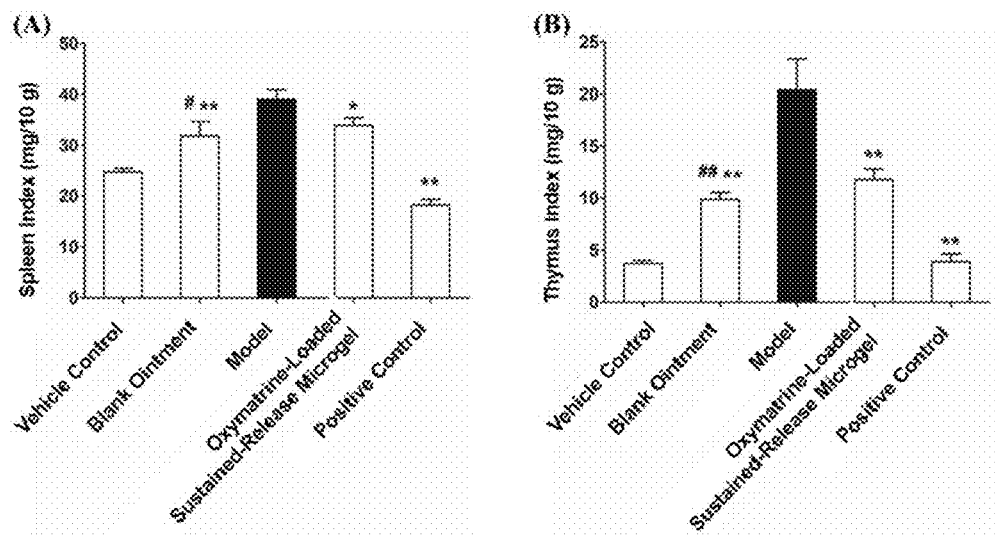
FIG. 12 is a graph showing the effect of the oxymatrine-loaded sustained-release microgel ointment on the spleen and thymus index of mice model of comorbid itch and pain. Inset A shows the result of the spleen index, and inset B shows the result of the thymus index.

FIG. 12 shows the effect of the oxymatrine-loaded sustained-release microgel ointment on the spleen and thymus index of mice model of comorbid itch and pain. Compared with the vehicle control group, the thymus index and spleen index of mice in the blank ointment group increased significantly ($p<0.05$ or 0.01). Compared with the model group, the thymus index and spleen index of mice in the blank ointment group, the oxymatrine-loaded sustained-release microgel ointment group and positive drug group all showed a very significant decrease ($p<0.05$ or 0.01).

Figure 13:
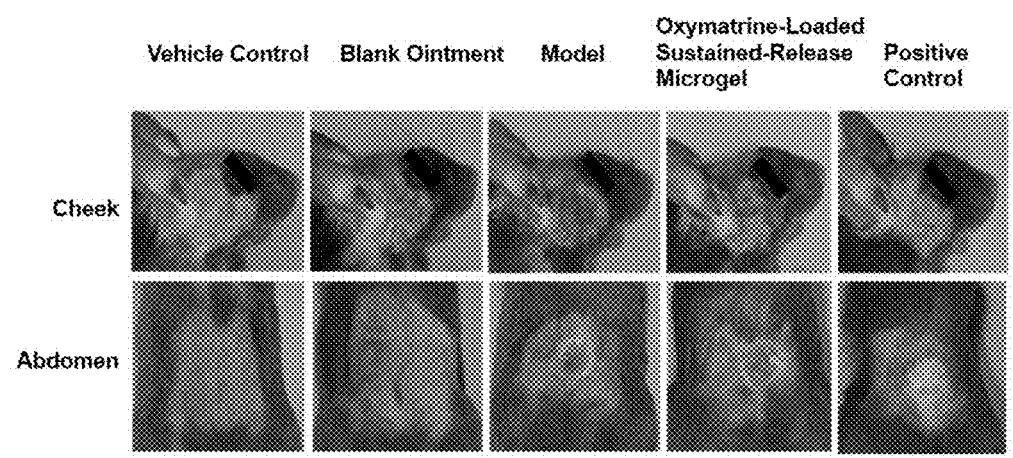
FIG. 13 is a graph showing the effect of the oxymatrine-loaded sustained-release microgel ointment on the challenged area of the right cheek skin and the sensitized area of the abdominal skin of mice model of comorbid itch and pain.

FIG. 13 shows representative pictures of the challenged area of the right cheek skin and the sensitized area of the abdominal skin of the mouse in the experiment of the oxymatrine-loaded sustained-release microgel ointment. It can be clearly seen from the figure that the cheeks and abdomen of mice in the vehicle control group and the blank ointment group were not significantly different. Compared with the model group, the oxymatrine-loaded sustained-release microgel ointment group, especially the positive drug group, had significantly improved cheek scabs. Some mice's scabs began to fall off. The redness and swelling of the challenged skin were reduced, and some disappeared completely.

Figure 14:
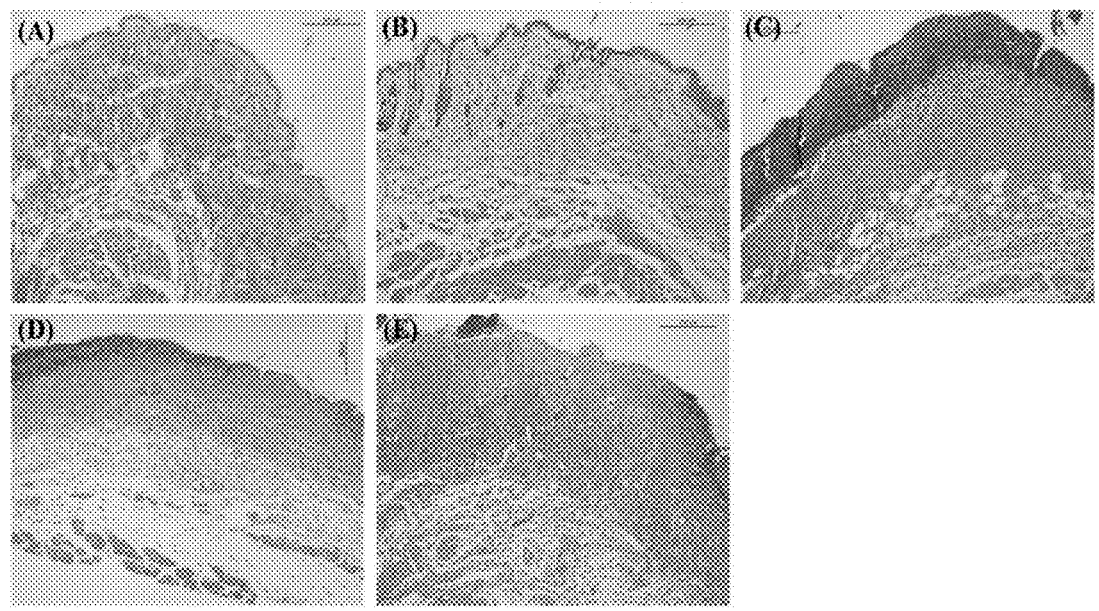
FIG. 14 shows the effect of the oxymatrine-loaded sustained-release microgel ointment on hematoxylin-eosin (HE) staining on the right cheek of mice model of comorbid itch and pain. A. vehicle control group. B. blank ointment group. C. model group. D. oxymatrine-loaded sustained-release microgel ointment group. E. positive drug group. The magnification is 100×.

FIG. 14 shows the results of HE staining of the challenged skin on the right cheek of the mouse in the experiment of oxymatrine-loaded sustained-release microgel ointment. Compared with the vehicle control group (A), the blank ointment group (B) had slightly thickened skin epidermis, but there was no damage to the deep skin structure. The skin epidermis in the model group (C) had severe hyperkeratosis, with the thickening of the stratum corneum and spinous cell layer, accompanied by scabs falling off. There was also seen lichen-like infiltration, deepened skin groove, and protruded skin ridges. The boundary between the epidermis and the dermis became unclear and a large number of lymphocytes infiltrated the upper part of the dermis. Compared with the model group, the epidermal thickness of the mice in the oxymatrine-loaded sustained-release microgel ointment group (D) and the positive drug group (E) was significantly reduced, the degree of inflammatory cell infiltration was reduced, and the skin pathology had a certain degree of improvement.

Figure 15:
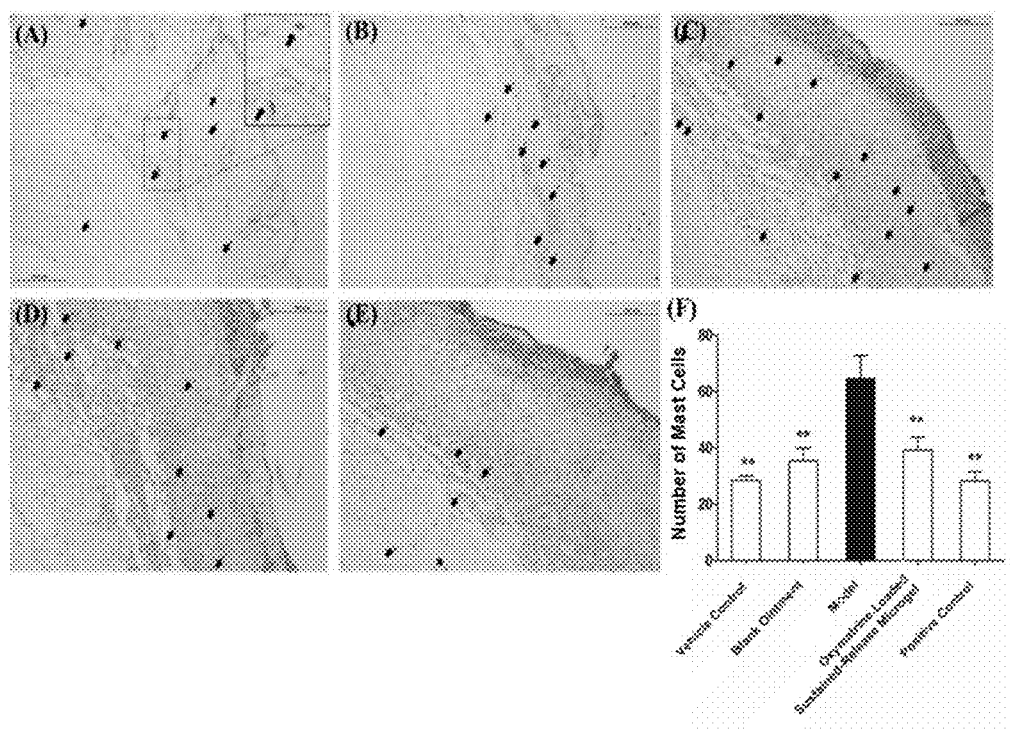
FIG. 15 is a graph showing the effect of the oxymatrine-loaded sustained-release microgel ointment on toluidine blue (TB) staining on the challenged area of the right cheek skin of mice model of comorbid itch and pain. A. vehicle control group, with the blue-purple spots in the magnified area of the red cage being the mast cells stained with toluidine blue. B. blank ointment group. C. model group. D. oxymatrine-loaded sustained-release microgel ointment group. E. positive drug group with a magnification of 100×. F. histogram of the number of mast cells in the cheek skin of mice in each group.

FIG. 15 shows the results of toluidine blue staining on the challenged skin of the right cheek of the mouse in the experiment of oxymatrine-loaded sustained-release microgel ointment. Compared with the vehicle control group (A), the blank ointment group (B) had no significant difference in the number of mast cells in the skin of mice. Compared with the blank gel group, mast cells were severely infiltrated in the cheek skin of the model group (C), and the number increased significantly ($p<0.01$). Compared with the model group, the number of mast cells in the cheek skin of mice in the oxymatrine-loaded sustained-release microgel ointment group (D) and the positive drug group (E) was significantly reduced ($p<0.01$).

CONCLUSION

First, we explored the optimal ratio of HTCC/HA and the preparation method through orthogonal experiments, and we prepared HTCC/HA nanoparticles with a particle size of about 150-350 nm and a potential of −30 to −20 mV. The particle had a spherical morphology and the particle size was relatively uniform, as observed under a transmission electron microscope. In addition, the influence of added drug amount on the drug loading of the nanoparticles was studied, and it was found that there is an optimal drug loading rate within a certain range, and that added drug amount is not simply proportional to the drug loading rate. When the ratio was 2:1, the internal drug loading rate of the HTCC/HA nanoparticles was 80%, and the distribution in the aqueous solution was 20%. Finally, in vitro release experiments showed that the release rate of the oxymatrine-loaded sustained-release microgel ointment can exceed 90% after 48 hours.

Then, the oxymatrine-loaded sustained-release microgel ointment was applied on the cheek once a day for 3 consecutive days during the challenging period of the mouse model with comorbid pain and itching. The results showed that the oxymatrine-loaded sustained-release microgel ointment could significantly reduce the number of cheek wiping behavior (pain sensation) and also the number of cheek scratching behavior (itching sensation). In addition, the oxymatrine-loaded sustained-release microgel ointment can significantly reduce the thickness of mouse cheek skinfold ($p<0.05$), and spleen and thymus index ($p<0.01$).

By analysis of the appearance of the cheeks and abdomen of each group of mice, the oxymatrine-loaded sustained-release microgel ointment improved scabs and reduce redness and swelling. The results of HE staining showed that the thickness of the skin epidermis of the mice in the oxymatrine-loaded sustained-release microgel ointment group was significantly reduced, the degree of inflammatory cell infiltration was reduced, and the skin damage was improved to a certain extent. The results of toluidine blue staining showed that the infiltration of mast cells in the skin of mice in the oxymatrine-loaded sustained-release microgel ointment group was significantly reduced, and the number of mast cells was reduced. In summary, the external use of oxymatrine-loaded sustained-release microgel ointment had the effects of treating histamine-independent pruritus, analgesia, and anti-inflammation.

The embodiments disclosed above are preferred embodiments of the present invention, but the present invention is not limited by the above-mentioned embodiments, and any other changes, modifications, substitutions, combinations, simplification and etc. made without departing from the spirit and principle of the present invention, should be an equivalent of the embodiment, and they are all included in the scope of the present invention.

What is claimed is:

1. A method for preparing a sustained-release microgel ointment with high drug loading, comprising steps of
    (1) mixing a 2-hydroxypropyltrimethyl ammonium chloride chitosan (HTCC) aqueous solution with a hyaluronic acid (HA) aqueous solution homogeneously to obtain an HTCC/HA microgel aqueous solution;
    (2) mixing a drug with the HTCC/HA microgel aqueous solution obtained from step (1), and concentrating the mixture; and
    (3) adding a thickener and stirring well to obtain the sustained-release microgel ointment with high drug loading;
    wherein, in step (1), a mass ratio of the HTCC to the HA is at 1:1 to 1:3, the HA has a molecular weight of $5.0\times10^4$ to $20.0\times10^4$ Dalton, the HTCC has a molecular weight of $2.0\times10^4$ to $20.0\times10^4$ Dalton, the HTCC aqueous solution has a concentration of 0.1 to 2.0 mg/mL, and the HA aqueous solution has a concentration of 0.1 to 2.0 mg/mL;
    wherein, the thickener in step (3) is hydroxypropyl methylcellulose; and
    wherein, step (1) is performed by adding the HTCC aqueous solution to the HA aqueous solution under stirring.

2. The method of claim 1, wherein, a mass ratio of the drug to the HTCC/HA microgel in step (2) is at 1:1 to 4:1; and the thickener in step (3) is added at 2% to 8% by weight based on the sustained-release microgel ointment with high drug loading.

3. The method of claim 2, wherein the drug in step (2) is at least one of an alkaloid and a flavonoid; and the concentrating step in step (2) is rotary evaporation.

4. The method of claim 3, wherein the alkaloid is at least one of oxymatrine, sophocarpine and oxysophocarpine; and the flavonoid is at least one of calycosin and maackiain.

5. The method of claim 1, wherein the sustained-release microgel ointment comprises a drug having an effect of treating histamine-independent pruritus and analgesia.

* * * * *